United States Patent [19]
Turner et al.

[11] Patent Number: 5,958,345
[45] Date of Patent: Sep. 28, 1999

[54] THIN FILM SAMPLE SUPPORT

[75] Inventors: D. Clark Turner; Arthur A. Robbins; Alisa A. Wilson, all of Orem, Utah

[73] Assignee: Moxtek, Inc., Orem, Utah

[21] Appl. No.: 08/818,168

[22] Filed: Mar. 14, 1997

[51] Int. Cl.[6] .................................................. B01L 9/00
[52] U.S. Cl. ..................... 422/104; 422/82.05; 422/102; 428/409; 435/301; 436/531; 436/535
[58] Field of Search ..................... 422/102, 104, 422/98, 82.05; 435/301; 436/531, 535; 428/409, 543

[56]     References Cited
       U.S. PATENT DOCUMENTS

| | | | |
|---|---|---|---|
| 4,560,599 | 12/1985 | Regen | 428/409 |
| 5,041,266 | 8/1991 | Fox | 422/102 |
| 5,458,852 | 10/1995 | Buechler | 422/58 |
| 5,544,218 | 8/1996 | Turner et al. | 378/208 |

*Primary Examiner*—Krisanne Thornton
*Attorney, Agent, or Firm*—Thorpe, North & Western, LLP

[57]             ABSTRACT

A sample support for holding for samples for use with an analysis instrument. The sample support is particularly beneficial for use with analysis instruments which rely on a beam of radiation or accelerated particles and a method for making the same is disclosed. The holder includes a frame with one or more orifices covered by a support surface, typically in the form of a thin polymer film. The film is divided into hydrophobic and hydrophilic portions to isolate precise positions where samples can be placed to intersect a probe beam during analysis.

26 Claims, 2 Drawing Sheets

THIN FILM SAMPLE SUPPORT

BACKGROUND OF THE INVENTION

1. Field of the Invention

The present invention relates to polymeric structures which are configured to position a sample in a precise location for chemical analysis. More particularly, the polymer film is provided with a central portion surrounded by an exterior portion, one of which is hydrophilic and the other of which is hydrophobic. When a sample is placed on the thin polymer film, the sample is placed on the central portion. The hydrophilic or hydrophobic exterior portion (depending on the characteristics of the liquid in which the chemical is suspended or dissolved) prevents the sample from spreading out beyond the hydrophilic portion, thereby ensuring that the chemical to be analyzed will be properly positioned when the liquid evaporates.

2. State of the Art

In order to conduct spectral analysis of chemicals (e.g. x-ray fluorescence, XRF), it is important to hold a very small sample in such a manner that the chemical is positioned within a radiation beam, etc., during the analysis. Various methods have been used to hold the chemical sample in the desired location. For example, U.S. Pat. No. 4,587,666 describes a method of making a sample cup with thick walls and a membrane to separate the liquid sample from the vacuum chamber of the XRF instrument. The membrane is large (1 to 2 inches) and must have a "perfectly flat horizontal face." The container can support a liquid or solid and separate it from the vacuum portion of the instrument while passing at least some of the illuminating and emitted radiation.

An alternative method of supporting a sample with a low vapor pressure in a device is to attach it to a thin, flat membrane and support the entire assembly in the vacuum chamber of the instrument. The probe beam can be electromagnetic radiation (e.g., x-rays) or particles (e.g., accelerated protons). For small samples, microbeams (diameters of less than 2 mm) have been used. This puts the support membrane under intense radiation which could lead to damage and failure.

The characteristics of the membrane are important for the analysis in the following ways, a partial list taken from Solazzi in his article entitled "X-ray Fluorescence Thin-Film Sample Support Materials," American Laboratory (1985), 17(11):3:

1. Relatively high degree of resistance to chemical attack.
2. Resistance to radiation damage such as embrittlement, thermal softening, etc.
3. Good sample retention strength so the dried sample does not fall off or blow off.
4. Freedom from impurities that may interfere with the analysis.
5. Thin, and yet strong enough to withstand handling.
6. A surface that is sufficiently smooth and even.

Support films typically limit the detection of small quantities of analyte because the films scatter photons or particles from the probe beam. In XRF, scattering is the limiting factor. In response, over the past 40 years workers have attempted (with limited success) to make thinner films of low atomic weight materials (carbon, nitrogen, oxygen, hydrogen and boron) having atomic weights less than fluorine. Examples are boron nitride as proposed by Prang, et al., ("Boron Nitride Sample Carriers for Total-Reflection X-ray Fluorescence," Spectrochemica Acta (1993), 48B: 153–161), and by Pauwels et al. ("Polyimide Substrate for Nuclear Targets," Nuclear Instruments and Methods (1979), 167: 109–112). The thicker the film, the more the film becomes a limiting factor in the analysis. Those skilled in the art will recognize that techniques for preparing thin polymer films (i.e. films of less than about 50 $\mu g/cm^2$) are well-known.

Many samples are solutions or suspensions. The solvent is typically evaporated (see Hannson et al., "A Non-Selective Preconcentration Technique for Water Analysis by PIXE," Nuclear Instruments and Methods in Physics Research, (1984), B3: 158–162 and Mangelson et al., "Particle Induced X-ray Emission Elemental Analysis: Sample Preparation for a Versatile Instrumental Method," Scanning Microscopy (1990), 4: 63–72). Flat sample holders are often made of a porous material (e.g. filter paper). Even though the sample droplet may be carefully placed, there remains ambiguity in the position of the sample after drying because of uncontrolled amounts of lateral diffusion and soaking of the solution which has been applied. Even when the film is smooth and impervious to liquid, the small sample may not dry exactly in its initial position because of droplet motion. Slight inhomogeneities in the surface tension of the film may induce the droplet to spread in an uncontrollable manner. Additionally, evaporation may deposit the solid at the edge of the evaporating droplet. These processes take an unknown portion of the sample out of the microscopic probe beam and invalidate the analysis.

Over the past 40 years, a long-felt need has become evident because all of the conventional approaches suffer from one or more of the following problems:

1. The position of the small, dry sample is uncertain (e.g., soaking on filter paper);
2. The sample falls off during handling;
3. The holder deteriorates because of radiation damage, high temperature or both; and
4. Upon drying, the holder allows the sample to clump in such a way that the probe beam and radiation emitted by the analyte do not correctly represent the quantity of sample.

This last problem arises because a large clump can severely attenuate the probe radiation (leaving some of the sample unexcited), or it can attenuate the emitted radiation. In addition, emission of one element in the sample can be absorbed by another and enhance the emission of the second, thus invalidating the analytical method. It is very difficult to correct for these effects from sample to sample because the clump size (and therefore the error) may vary from place to place due to random amounts and positions of clumping. A thin film of the analyte minimizes these errors and allows for a dependable calibration of their extent. The severity of this self-absorption problem scales as the absorption coefficient, so the problem can be largely ignored for highly transparent samples.

It would be advantageous if there were precisely located positions on the film where the sample droplet would remain during evaporation. The films should be free of any interfering contaminants. In addition, the film should hold the dry sample in position during handling and analysis.

One solution to such problems is set forth in U.S. Pat. No. 5,544,218. The patent relates to a thin film sample support which has small concave impressions formed therein for holding the samples. While the sample support works well, forming concave impressions in the thin film can be difficult. Because the films are often less than 50 $\mu g/cm^2$, the films are easily torn or punctured.

Thus, there is a need for a polymer film sample support which provides precisely located positions on the film where the sample droplet will remain during evaporation. The films should be free of any interfering contaminants. In addition, the film should hold the dry sample in position during handling and analysis. These and other advantages are achieved with the instant invention which is described in more detail to follow.

SUMMARY OF THE INVENTION

It is an object of the present invention to provide a polymer film sample holder which increases the certainty of the position of the small, dry sample.

It is another object of the invention to provide a thin polymer film sample holder which decreases the risk that a sample may fall off during handling.

It is yet another object of the present invention to provide a thin polymer film sample holder which minimizes sample clumping so that the radiation emitted by the analyte more correctly represents the quantity of the sample.

It is yet another object of the invention to provide a sample holder that does not interfere with radiation absorption and emission of the analyte.

It is still another object of the present invention to provide such a polymer film which has an analyte holding portion with a surface (areal) density of less than 50 $\mu g/cm^2$.

The above and other objects of the invention are realized in specific illustrated embodiments of a polymer film sample support including a polymer film having a central portion and an exterior portion surrounding the central portion. One of the central and exterior portions is formed of a hydrophobic material, while the other is formed from a hydrophilic material. The hydrophilic and hydrophobic materials are configured to prevent spreading of the sample outside of a desired position.

In accordance with one aspect of the present invention, a hydrophobic exterior portion is positioned about a hydrophilic central portion. When a hydrophilic liquid having a chemical to be analyzed suspended or dissolved therein is placed on the hydrophilic central portion of the film, the hydrophobic exterior portion forms a perimeter which prevents unwanted spreading of the liquid as it dries. Thus, once the liquid has dried, the chemical to be analyzed will be disposed at the central portion instead of having spread to some unknown extent.

In accordance with another aspect of the present invention, the hydrophilic material is used to form an exterior portion which surrounds a hydrophobic central portion. Thus, when a chemical to be analyzed is dissolved or suspended in a hydrophobic liquid, the liquid is able to dry on the hydrophobic central portion while spread of the liquid is prevented by the hydrophilic exterior portion disposed thereabout.

In accordance with another aspect of the present invention, at least the portion of the film forming the central portion is formed of a thin film (i.e. typically less than about 50 $\mu g/cm^2$). Having a thin film formed in the central portion helps to prevent interference with analysis of the analyte. A number of polymeric, film-forming materials are available, including organic polymers, inorganic polymers (typically based on silicates), and even carbonized films made from such materials as rayon.

In order to form a thin film having a hydrophilic portion surrounded by a hydrophobic portion, several techniques may be followed. Because many thin films are typically hydrophilic, the desired hydrophilic/hydrophobic pattern may be easily achieved by coating the hydrophilic film with a hydrophobic coating. The hydrophobic coating may then be etched away at the desired location, thereby leaving a hydrophilic central portion surrounded by a hydrophobic exterior portion. Spread of the liquid containing the analyte is inhibited both by the hydrophobic coating, and the slight rise about the perimeter of the hydrophilic portion formed by the hydrophobic coating.

In the alternative to the above, a hydrophilic central portion could be formed by placing a small layer of hydrophilic material on top of a hydrophobic polymer film, or on top of a hydrophobic coating on a hydrophilic film. Furthermore, a hydrophobic ring could be formed on a hydrophilic thin film to isolate part of the hydrophilic film at a desired location. Regardless of which method is used for making the thin film, a hydrophilic liquid disposed thereon will have less tendency to spread from the desired location due to the hydrophobic barrier which surrounds it.

When forming a polymer film sample support for use with a hydrophobic liquid, the different methods for forming the sample support may be used. For example, a sample support may be made using a hydrophobic film and coating the film with a hydrophilic layer which is either configured to leave a hydrophobic central section, or by etching away part of the hydrophilic coating to leave a hydrophobic central portion of a desired size.

While numerous layering combinations can be used to achieve a desired hydrophobic/hydrophilic configuration for the film, it is important to remember that exceptionally thick films have a tendency to interfere with analysis. Therefore, it is preferred to keep the number of layers to a minimum.

There are several methods of etching the upper layer to leave the desired sample spot. A droplet of solvent or some reactive material, such as a mineral acid, can be placed on the spot and rinsed off when the etching is complete. Some polymers will sublime off the base if heated, say with a spot of laser light. If the upper layer is a photoresist, it can be exposed and processed to lift of the photo resist from the desired spot. These two methods using heat or light can position the spot with greater precision than the placement of droplets can. In addition, a combination of reactive fluid and light can be used to promote a photochemical reaction in the polymer. This may remove the polymer, or it may change its properties (e.g. change it from hydrophilic to hydrophobic or the converse). In the latter case, no more than one layer of polymer is necessary if the process that forms the desired spot does not seriously weaken the film.

Yet another method of etching makes use of a colony of bacteria that excrete chemicals that etch the upper layer of film. The colonies conveniently grow in a round spot. There must be adequate nutrient for the growth, and the colony should be washed off before the film is used to hold a sample of analyte.

Converse to etching, a spot of the proper hydrophilicity can be grown on the film. Likewise, proper masking can allow spots of metals and certain other materials to be placed by physical vapor deposition or chemical vapor deposition. For example, aluminum can be evaporated. It spontaneously grows an oxide coating which can be made acidic or basic (both hydrophilic) by chemical treatment. Furthermore, a plasma treatment can be used to change the hydrophilicity of some materials.

A final treatment of the central spot is desirable in cases where the analyte must be induced to nucleate crystallites that are well distributed rather than clumped. Imperfections in the film provide nucleation centers. These imperfections can be physical (e.g. lattice defects, terraces, screw dislocations, etc.) or they could be microcrystals of a material compatible with the crystal structure of the analyte. These microcrystals could be embedded in the polymer, or placed on top and held by Van der Waals and similar forces. Finely ground glass is known to nucleate many types of crystals.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
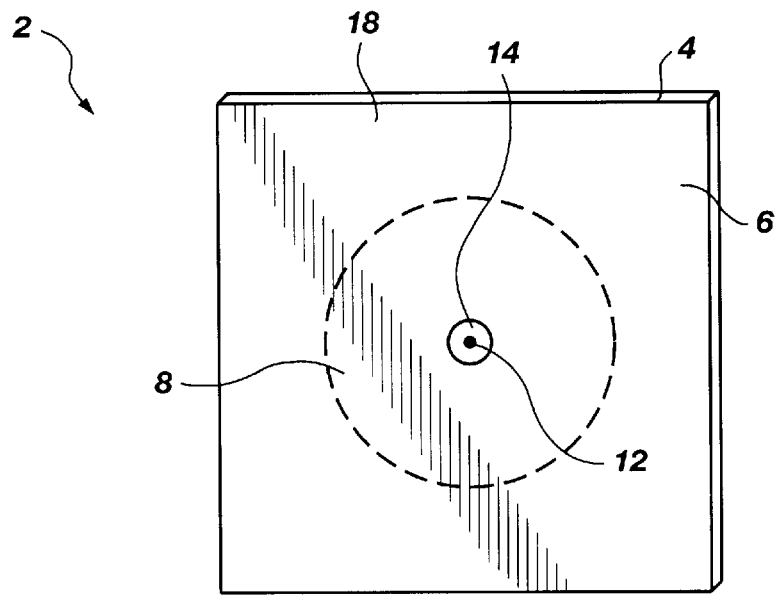
FIG. 1 shows a frame having one surface covered with a thin film that is marked in the center to receive a liquid sample.
Figure 2:
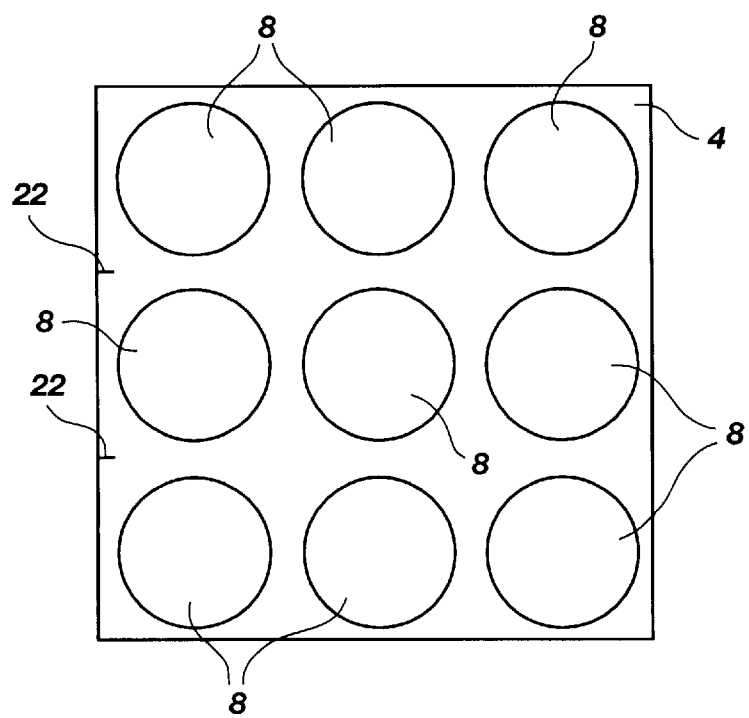
FIG. 2 shows a single frame having nine orifices over which the thin film may be supported while the chemicals disposed on the film are being analyzed.

Referring to FIGS. 1 and 2, there is shown a sample holder, generally indicated at 2, for use in analytical instruments where a small amount of analyte must be suspended in an irradiating beam of particles or electromagnetic radiation. The particles are typically electrons, protons, neutrons or alpha particles. The electromagnetic radiation could come from any portion of the spectrum (gamma rays to infrared wavelengths). The invention is especially suited to instruments using microbeams (i.e. beams of very small cross section). The spectrometers most commonly used for quantitative analysis are x-ray fluorescence spectrometers (XRF), proton induced x-ray emission spectrometers (PIXE) and Fourier transform infrared spectrometers (FTIR). The invention is also useful as a support for nuclear targets, nuclear strippers, and filters in more general types of beam experiments.

The sample holder 2 of FIG. 1 includes a frame 4 which supports a thin polymer film 6. The frame 4 circumscribes one or more orifices 8 so that the frame will not interfere with analysis on a sample 12 which is placed on the film above an approximate center of the orifice. The orifice(s) 8 are large enough to allow a probe beam of radiation to strike the sample 12 on the film 6 without striking the frame 4, but small enough that the frame provides ample support to the film.

The film 6 has a central portion 14, and an exterior portion 18 disposed to circumscribe the central portion. One of the central and exterior portions is formed of a hydrophilic material, while the other portion is formed of a hydrophobic material. Which portion is formed from which material depends on the liquid used to carry the analyte. If the liquid in which the analyte is dissolved or suspended is hydrophilic, then the central portion 14 of the film 6 will be made of a hydrophilic material, and the exterior portion 18 of the film will be made from a hydrophobic material. In contrast, if the liquid to be used will be hydrophobic, the central section 14 will be hydrophobic and the exterior portion 18 will be hydrophilic.

By matching the central portion 14 of the film 6 to the characteristics of the liquid and by providing an exterior portion 18 made from a material having the opposite characteristics, the liquid containing the sample is inhibited from spreading out while it dries, and the chemical to be analyzed remains at the desired location on the film. Because this location is disposed at an approximate center of the orifice 8 in the frame 4, the frame will generally not interfere with the analysis.

Typically, the hydrophobic or hydrophilic central portion 14 will have a diameter of about 2 mm, while the orifices 8 in the frame 4 will have a diameter of about 10 mm. The frame 4 can be made of metal, polymer, ceramic or any solid material with sufficient stability to support the film 6 during transport or use. Of course, the orifices 8 can be placed for convenience, e.g., to match the sample transport mechanism of the instrument for correct positioning of each sample, and may include reference points, such as those indicated at 22 in FIG. 2.

In a preferred embodiment, a sample of material that luminesces in the irradiating beam is placed in one of the central portions 14 to allow precise alignment within the probe beam. The analytical equipment can then automatically know the location of other samples.

As is well known in the art, there are some applications in which the frame 4 must not contaminate the vacuum chamber of the instrument by emitting gases or vapors. Additionally, the frame 4 must not shed particles. In such situations, aluminum sheet (1.6 mm thick) is the preferred material for forming the frame 4.

Referring specifically to FIG. 2, the top of the frame 4 (or at least each orifice) would be covered with a thin polymer film 6 (FIG. 1), the central portion 14 of which is preferably less than 50 $\mu g/cm^2$. Because thick films scatter sufficient radiation to degrade the performance of the instrument, the film must be pure and must be made of light elements (e.g., H, B, C, N, O). Under these conditions, the film is not a source of greater noise than that inherent in the instrument.

The film 6 of the preferred embodiment consists of pure polyimide with thickness in the previously specified range. However, other films may be used, such as polyvinyl formal, polycarbonate, polypropylene, polyethylene, parylene, PROLENE™ (isotactic polypropylene) and MYLAR™. Which material is preferred will depend primarily on whether the liquid to be used is hydrophobic or hydrophilic, and the configuration of the film with respect to forming a hydrophobic or hydrophilic central portion 14 with an exterior portion 18 of the opposite characteristics.

Figure 3:
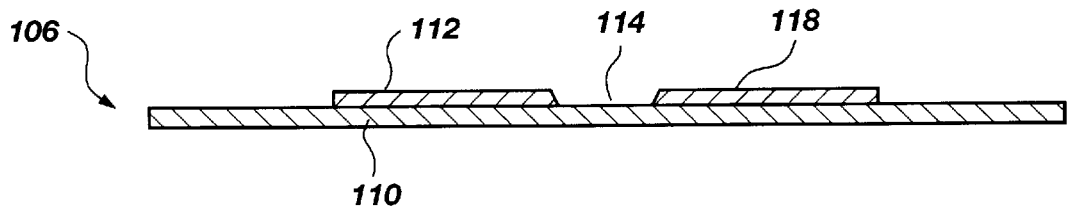
FIG. 3 shows a close-up, cross-sectional view of one embodiment of the present invention for use with a hydrophilic liquid.

Turning now to FIG. 3, there is shown a close-up, cross-sectional view of one embodiment of the thin film, generally indicated at 106, of the present invention. The thin film 106 is formed with a base layer 110 and a secondary layer 112. In the embodiment shown in FIG. 3, the base layer 110 is formed from a polymer film which is generally hydrophilic.

The secondary layer 112 disposed on the base layer 110 is formed from a hydrophobic material. The base layer 110 and the secondary layer 112 are configured to provide a hydrophilic central portion 114, which is substantially surrounded by a hydrophobic exterior portion 118.

The central portion 114 can be formed in several different ways. One relatively simple method is to coat the hydrophilic base layer 110 with a secondary layer 112 in the form of a hydrophobic coating. A portion of the hydrophobic secondary layer 112 is then etched or otherwise cut way, thereby exposing a hydrophilic central portion 114.

An alternative to the above is to simply form the secondary layer 112 from a thin film having a hole therein. When the film is placed on the base layer 110 to form the secondary layer 112, the hole formed therein exposes a portion of the base layer and defines the hydrophilic central portion 114.

Figure 4:
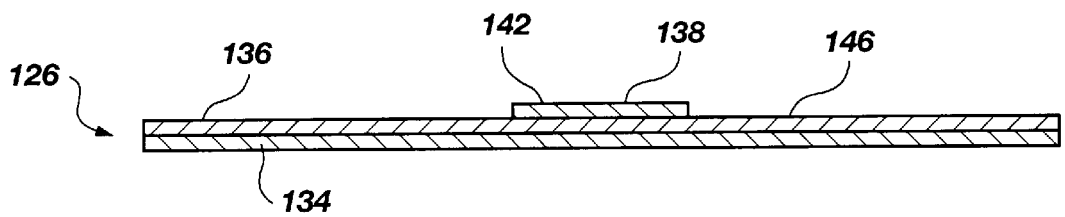
FIG. 4 shows a close-up, cross-sectional view of an alternate embodiment of the present invention for use with a hydrophilic liquid.

Referring now to FIG. 4, there is shown a close-up, cross-sectional view of another embodiment of a thin film, generally indicated at 126, configured with hydrophobic and hydrophilic portions to provide an improved sample support. Specifically, the thin film 126 is formed with a base layer 134, a secondary layer 136, and a tertiary layer 138. The base layer 134 is formed from a hydrophilic film. The secondary layer 136 is formed from a hydrophobic film. And the tertiary layer 138 is formed from a hydrophilic film. Thus, the tertiary layer 138 forms a hydrophilic central portion 142, while the secondary layer 136 forms a hydrophobic exterior portion 146.

Unlike the embodiment shown in FIG. 3, the embodiment of FIG. 4 avoids the necessity of forming the secondary layer with a hole, or of etching a hole into the secondary layer to form the central section. However, because the tertiary layer 138 which forms the hydrophilic central section 142 is disposed on top of the secondary layer 136 forming the hydrophobic exterior portion 146, a hydrophilic liquid will have a slightly greater tendency to spread out during drying.

Figure 5:
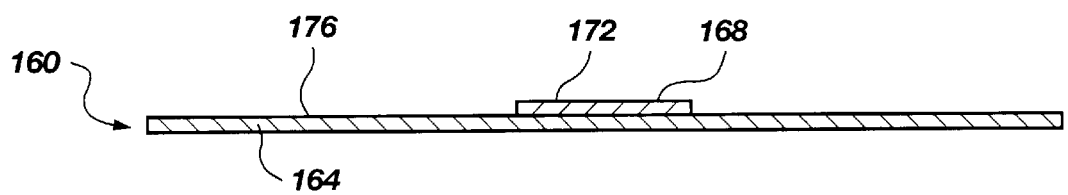
FIG. 5 shows a close-up, cross-sectional view of an embodiment of the present invention for use with a hydrophobic liquid.

Turning now to FIG. 5, there is shown an alternate embodiment of the present invention. The thin film, generally indicated at 160, includes a hydrophilic base layer 164, and a hydrophobic secondary layer 168. The secondary layer 168 is much smaller than the base layer 164 and forms a hydrophobic central section 172. The base layer 164 extends outwardly from the central portion 172 and forms an exterior portion 176 which surrounds the central portion. If a hydrophobic liquid is disposed on the central portion 172, it will be repelled by the hydrophilic exterior portion 176, thereby encouraging its contents to remain on the central portion while the liquid dries.

Figure 6:
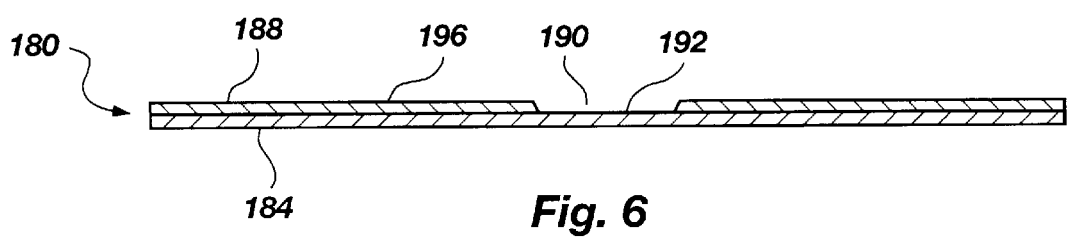
FIG. 6 shows a close-up, cross-sectional view of another embodiment of the present invention for use with a hydrophobic liquid.

Turning now to FIG. 6, there is shown yet another embodiment of the present invention. Similar to the embodiment shown in FIG. 3, the embodiment of the thin film sample support shown in FIG. 6 and generally indicated at 180, includes a base layer 184 and a secondary layer 188. A void 190 is formed in the secondary layer 188 by way of etching or some other process. The void 190 exposes the base layer 184 to form a central portion 192 surrounded by an exterior portion 196. However, unlike the embodiment shown in FIG. 3, the thin film 180 shown in FIG. 6 uses a hydrophobic base layer 184 and a hydrophilic secondary layer 188. Thus, when the void is formed to expose the base layer 184, a hydrophobic central portion 192 is formed, surrounded by a hydrophilic exterior portion 196.

While the base, secondary and tertiary (when provided) layers come in a wide variety of thicknesses, the nature of the chemical analysis strongly favors configurations in which the surface density of the thin film is no greater than 50 $\mu g/cm^2$ in the central portion. Outside of the central portion, however, films of greater density can be used. In configurations such as those shown in FIGS. 3 and 6, using a thicker film in the part of the exterior portion (118 and 196) formed by the secondary layer may further assist in keeping the analyte in the desired location.

Once the polymer film is formed, it is placed on a support frame, such as those discussed with respect to FIGS. 1 and 2. The support frame holds the thin film generally taut, and prevents damage to the film while it is being handled for purposes of analysis. While individual segments can be used on the support frame, the thin films described herein will typically be made with several central and exterior portions—nine being a very typical number—on one large sheet of film. Having several central/exterior portion configurations supported by a single frame makes handling much easier and more economical.

Another method starts with a hydrophobic base layer such as base layer 184. A small spot of hydrophilic polymer is placed at the desired location on the base layer 184 by directing a jet of monomer gas (e.g. paraformaldehyde) at the heated central portion 192, or by using light in that portion to yield photopolymerization. Suitable light sources include UV lasers (excimer, He-Cd, quadrupled Nd:YAG) that are absorbed by the polymer, and whose photons have sufficient energy to cause polymerization.

Thus there is disclosed an improved thin film sample support. Those skilled in the art will appreciate numerous modifications which can be made without departing from the scope and spirit of the present invention. The appended claims are intended to cover such modifications.

What is claimed is:

1. A sample holder for retaining a liquid sample in a localized region and configured for subsequent analytical processing in a beam of electromagnetic radiation, the sample holder comprising:

a substantially planar sample support surface for providing a localized region for receiving a test sample and having a central portion and an exterior portion disposed to substantially surround the central portion, one of the central portion and the exterior portion having a hydrophilic surface, and the other of the central portion and the exterior portion having a hydrophobic surface, the central and exterior portions of the sample support surface being formed of a material which resists spectral contamination.

2. The sample holder of claim 1, wherein the sample support surface is configured to use as part of an analytical processing system utilizing particle beams.

3. The sample holder of claim 2, wherein the sample support surface is formed by a polymer film.

4. The sample holder of claim 1, wherein the support surface has a composition having atomic components, and wherein each atomic component of the support surface has an atomic number less than that of fluorine.

5. The sample holder of claim 1, wherein the holder further comprises:

a support frame defining at least one orifice for holding the sample support surface and maintaining the sample support surface in a generally planar orientation, the sample support surface being disposed on the frame with the central portion disposed in alignment with the orifice such that an x-ray beam may pass through the central portion without contacting the frame.

6. The sample holder of claim 1, wherein the sample support surface is formed of a polymer film and wherein the central portion of the film has a surface density of less than about 50 µg/cm$^2$.

7. The sample holder of claim 1, wherein the central portion is configured to be subjected to x-ray electromagnetic energy, while maintaining nominal scattering of x-rays.

8. The sample holder of claim 1, wherein the central portion has a diameter of 2 mm or less.

9. The sample holder of claim 1, wherein the support surface comprises a polymer film having a plurality of central portions, each central portion having a hydrophilic surface, and each central portion being substantially surrounded by a exterior portion having a hydrophobic surface.

10. The sample holder of claim 1, wherein the support surface comprises a polymer film having a plurality of central portions, each central portion having a hydrophobic surface, and each central portion being substantially surrounded by a exterior portion having a hydrophilic surface.

11. The sample holder of claim 1, wherein the support surface comprises a polymer film which is formed of at least one of the group consisting of polyvinyl formal, polyimide, polycarbonate, polypropylene, polyethylene, parylene and isotactic polypropylene.

12. The sample holder of claim 11, wherein the film is at least partially formed of polyimide.

13. The sample holder of claim 5, wherein the support frame is comprised of a composition (i) which provides structural rigidity adapted for applications involving exposure of the sample holder to an analytical beam,, and (ii) which has a sufficiently low vapor pressure to preclude contamination of a test environment.

14. The sample holder of claim 1, further comprising positioning means disposed on the sample support surface for alignment with respect to an analytical beam.

15. The sample holder of claim 14, wherein the positioning means comprises a material that luminesces in an irradiating beam disposed on the central portion of the support surface.

16. The sample holder of claim 3, wherein the polymer film comprises a base layer formed from a hydrophilic material as the central portion, and a secondary layer formed of a hydrophobic material as the exterior portion.

17. The sample holder of claim 16, wherein a void is etched in the secondary layer to expose the hydrophilic material of the base layer, thereby forming a hydrophilic central portion surrounded by a hydrophobic exterior portion.

18. The sample holder of claim 1, wherein the support surface comprises a polymer film having a base layer formed from a hydrophobic material as the central portion and a secondary layer formed of a hydrophilic material as the exterior portion.

19. The sample hold of claim 18, wherein a void is etched in the secondary layer to expose the hydrophobic material of the base layer, thereby forming a hydrophobic central portion surrounded by a hydrophilic exterior portion.

20. A sample holder for retaining a liquid sample in a localized region and configured for subsequent analytical processing in a beam of electromagnetic radiation, the sample holder comprising:

a substantially planar sample support surface for providing a localized region for receiving a test sample and having a substantially planar base layer and a substantially planar secondary layer disposed on the base layer to provide a central portion and an exterior portion substantially surrounding the central portion, one of the base or secondary layers having a hydrophilic surface, and the other of the base or secondary layers having a hydrophobic material such that one of the central or exterior portions has a hydrophilic surface, and the other of the central or exterior portions has a hydrophobic surface, the base and secondary layers being formed of a material which resists spectral contamination.

21. The sample holder of claim 20, wherein the secondary layer has a hole formed therein exposing a portion of the base layer such that the secondary layer forms the exterior portion and the base layer forms the central portion.

22. The sample holder of claim 20, wherein the base layer is a generally hydrophilic polymer film and the second layer is a generally hydrophobic coating disposed on the hydrophilic polymer film; and further comprising a hole formed in the hydrophobic coating of the secondary layer to expose a portion of the hydrophilic base layer.

23. The sample holder of claim 20, wherein the base layer is a generally hydrophobic film and the second layer is a generally hydrophilic film disposed on the hydrophobic film; and further comprising a hole formed in the hydrophilic film of the secondary layer to expose a portion of the hydrophobic base layer.

24. The sample holder of claim 20, wherein the base layer is a generally hydrophilic film and the second layer is a generally hydrophobic film disposed on the hydrophilic film, the hydrophobic film forming the exterior portion; and further comprising a tertiary layer disposed on the secondary layer and forming the central portion with the secondary layer surrounding the tertiary layer, the tertiary layer being a generally hydrophilic film.

25. The sample holder of claim 20, wherein the secondary layer is disposed on the base layer with the base layer surrounding the secondary layer such that the base layer forms the exterior portion and the secondary layer forms the central portion.

26. The sample holder of claim 20, wherein the base layer is a generally hydrophilic film and the second layer is a generally hydrophobic film disposed on the hydrophilic polymer film with the hydrophilic film of the base layer surrounding the hydrophobic film of the secondary layer.

* * * * *